US009322786B2

(12) United States Patent
Takami

(10) Patent No.: US 9,322,786 B2
(45) Date of Patent: Apr. 26, 2016

(54) SOLAR CELL INSPECTION APPARATUS AND SOLAR CELL PROCESSING APPARATUS

(75) Inventor: Yoshio Takami, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/377,725

(22) PCT Filed: Feb. 10, 2012

(86) PCT No.: PCT/JP2012/053128
§ 371 (c)(1),
(2), (4) Date: Oct. 28, 2014

(87) PCT Pub. No.: WO2013/118296
PCT Pub. Date: Aug. 15, 2013

(65) Prior Publication Data
US 2015/0160138 A1    Jun. 11, 2015

(51) Int. Cl.
*G01N 21/88* (2006.01)
*G01N 21/95* (2006.01)
(Continued)

(52) U.S. Cl.
CPC ........... *G01N 21/8803* (2013.01); *G01M 11/00* (2013.01); *G01N 21/8806* (2013.01);
(Continued)

(58) Field of Classification Search
CPC .......... G01N 2201/02; G01N 2201/04; G01N 2201/061
USPC ................................. 356/51, 237.2
See application file for complete search history.

(56) References Cited

U.S. PATENT DOCUMENTS 5,197,105 A * 3/1993 Uemura ............... G01N 21/956
348/126
5,268,735 A    12/1993 Hayashi
(Continued)

FOREIGN PATENT DOCUMENTS

JP    04-233440 A    8/1992
JP    07-094563 A    4/1995
(Continued)

OTHER PUBLICATIONS

International Search Report, w/ English translation thereof, issued in International Application No. PCT/JP2012/053128 dated May 15, 2012.

*Primary Examiner* — Roy M Punnoose
(74) *Attorney, Agent, or Firm* — McDermott Will & Emery LLP

(57) ABSTRACT

An inspection apparatus 1 for solar cells 100 includes: a visible light source 11 adapted to irradiate visible light; a CCD camera 15 adapted to measure a reflection image based on the visible light reflected by an antireflective film of a solar cell 100; an infrared light source 13 adapted to irradiate the solar cell 100 with infrared light; and a CCD camera 16 adapted to measure a transmission image based on the infrared light transmitting through the solar cell 100. In the inspection apparatus 1, as a result of comparing the reflection image and the transmission image with each other, of areas respectively appearing as bright spots in the reflection image, an area appearing as a dark spot in the transmission image is determined as an area including a particle, whereas of the areas respectively appearing as the bright spots in the reflection image, an area other than the area determined as the area including the particle is determined as an area including a pinhole.

7 Claims, 12 Drawing Sheets

(51) Int. Cl.
  *H02S 50/10* (2014.01)
  *G01M 11/00* (2006.01)
  *H01L 31/18* (2006.01)
  *G01N 21/894* (2006.01)

(52) U.S. Cl.
  CPC ........ *G01N21/9501* (2013.01); *G01N 21/9505* (2013.01); *H01L 31/18* (2013.01); *H02S 50/10* (2014.12); *G01N 21/894* (2013.01); *G01N 2201/02* (2013.01); *G01N 2201/04* (2013.01); *G01N 2201/061* (2013.01)

(56) References Cited

U.S. PATENT DOCUMENTS

| | | | |
|---|---|---|---|
| 6,540,416 B2 * | 4/2003 | Edgar | G03C 5/261 355/27 |
| 8,154,718 B2 * | 4/2012 | Graf | G01N 21/59 356/237.5 |
| 2003/0142975 A1 * | 7/2003 | Edgar | G03C 5/261 396/567 |
| 2006/0278831 A1 | 12/2006 | Matsumoto et al. | |
| 2011/0014725 A1 | 1/2011 | Abiko et al. | |

FOREIGN PATENT DOCUMENTS

| | | |
|---|---|---|
| JP | 10-246705 A | 9/1998 |
| JP | 2002-122552 A | 4/2002 |
| JP | 2004-151622 A | 5/2004 |
| JP | 2006-351669 A | 12/2006 |
| JP | 2007-294604 A | 11/2007 |
| JP | 2010-019731 A | 1/2010 |
| JP | 2010-054377 A | 3/2010 |
| WO | 20091096114 A1 | 8/2009 |

* cited by examiner

SOLAR CELL INSPECTION APPARATUS AND SOLAR CELL PROCESSING APPARATUS

CROSS-REFERENCE TO RELATED APPLICATIONS

This application is the U.S. National Phase of PCT/JP2012/053128 filed Feb. 10, 2012 the subject matter of which is incorporated herein by reference in entirety.

TECHNICAL FIELD

The present invention relates to an inspection apparatus for solar cells deposited with an antireflective film, and to a solar cell processing apparatus using the inspection apparatus for solar cells.

BACKGROUND ART

In a solar cell production process, visual inspection for inspecting cracking, chipping, pattern defects, deposited film defects, and the like of solar cells, and internal inspection for inspecting cracks and voids occurring inside solar cells are performed.

Patent Literature 1 discloses a defect inspection apparatus that inspects a defect in the surface of a semiconductor wafer by irradiating the semiconductor wafer with a laser beam from a laser light source, and also imaging an optical image reflected by the surface of the semiconductor wafer by an imaging device to extract the defect from image data on the semiconductor wafer imaged by a defect detecting part.

Also, Patent Literature 2 discloses an infrared inspection apparatus that irradiates a semiconductor wafer with infrared rays from an infrared light source, and also images infrared rays transmitting through the semiconductor wafer by an infrared camera. This infrared inspection apparatus is configured to detect a microcrack inside the semiconductor wafer by utilizing the difference in transmission state of the infrared rays between an abnormal part such as a crack and a polysilicon substrate part.

CITATION LIST

Patent Literature

Patent Literature 1: JP-A2002-122552
Patent Literature 2: JP-A2006-351669

SUMMARY OF INVENTION

Technical Problem

In a solar cell manufacturing process, after the deposition of an antireflective film, the deposited state of the film is inspected. Then, if the solar cell is determined as a non-defective product electrode printing and firing are performed on the solar cell. As the antireflective film, of the crystal silicon solar cell, a SiN (silicon nitride) film is deposited by a film deposition apparatus such as a plasma CVD apparatus using a vacuum chamber. After the film deposition is performed on a number of solar cells, many particles are accumulated inside the vacuum chamber of the deposition apparatus. In the film deposition process, steps of evacuation, gas introduction, film deposition, and ventilation are repeatedly performed, and therefore the probability of falling particles on the surface of the solar cells before or after the film deposition process increases.

In the case where particles have fallen on the surface of the solar cells before the film deposition process, and the antireflective film is deposited in this state, small areas where the antireflective film is not deposited are formed on the surfaces of some of the solar cells as pinholes in the film. On the other hand, in the case where particles fall on the surface of the solar cells after the film deposition process, the particles are so-called fall-on particles that are foreign substances placed on the surface of the antireflective film.

Usually, for a solar cell after the deposition of an antireflective film, as with Patent Literature 1 described above, fall-on particles on the film and pinholes in the film are both detected as some kind of point defects by measuring a visible light-based reflection image in a visual inspection apparatus. Then, in the case where the number of the point defects or a total area of the point defects reaches or exceed a preset value, the solar cell is recognized as a defective product and removed from a production line since both defects are indistinctive.

Of the point defects described above, the pinholes in the film are difficult to repair because there actually exist undeposited areas in the film, but the fall-on particles on the film can be removed from the antireflective film which has no defect, and therefore a solar cell having such fall-on particles can be used as a normal solar cell product. In the case of removing such a normal, non-defective solar cell from a production line by accident as a defective product, the problem of reducing production efficiency occurs.

This invention is made in order to solve the above problem, and an object thereof is to provide a solar cell inspection apparatus and solar cell processing apparatus that make it possible to improve production efficiency by distinguishing the solar cell which has a foreign substance on the film and a pinhole in the film.

Solution to Problem

An invention according to a first aspect of the present invention is a solar cell inspection apparatus adapted to inspect a solar cell deposited with an antireflective film, and the solar cell inspection apparatus includes: visible light irradiation means adapted to irradiate visible light to the solar cell from an antireflective film side of the solar cell; reflection image measuring means adapted to measure a reflection image based on the visible light that is irradiated from the visible light irradiation means and reflected by the antireflective film of the solar cell; infrared light irradiation means adapted to irradiate infrared light from a side opposite to the antireflective film of the solar cell; transmission image measuring means adapted to measure a transmission image based on the infrared light that is irradiated from the infrared light irradiation means and transmits through the solar cell; comparison means adapted to compare the reflection image measured by the reflection image measuring means and the transmission image measured by the transmission image measuring means with each other; and determination means adapted to determine, of areas respectively appearing as bright spots in the reflection image, an area appearing as a dark spot in the transmission image as an area including a foreign substance present on the antireflective film, and also determine, of the areas respectively appearing as the bright spots in the reflection image, an area other than the area determined as the area including the foreign substance as an area including a pinhole formed in the antireflective film.

An invention according to a second aspect of the present invention is the invention according to the first aspect, wherein the visible light irradiation means and the infrared light irradiation means simultaneously irradiate one surface and the other surface of the solar cell with the visible light and the infrared light, respectively, and the solar cell inspection apparatus includes a beam splitter adapted to: receive the visible light reflected by the antireflective film of the solar cell and the infrared light transmitting through the solar cell; guide the visible light reflected by the antireflective film of the solar cell to the reflection image measuring means, and also guide the infrared light transmitting through the solar cell to the transmission image measuring means.

An invention according to a third aspect of the present invention is a solar cell processing apparatus adapted to process a solar cell deposited with an antireflective film, and the solar cell processing apparatus includes an inspection apparatus having; visible light irradiation means adapted to irradiate visible light from an antireflective film side of the solar cell; reflection image measuring means adapted to measure a reflection image based on the visible light that is irradiated from the visible light irradiation means and reflected by the antireflection film of the solar cell; infrared light irradiation means adapted to irradiate infrared light from a side opposite to the antireflective film of the solar cell; transmission image measuring means adapted to measure a transmission image based on the infrared light that is irradiated from the infrared light irradiation means and transmitting through the solar cell; comparison means adapted to compare the reflection image measured by the reflection image measuring means and the transmission image measured by the transmission image measuring means with each other; and determination means adapted to determine, of areas respectively appearing as bright spots in the reflection image, an area appearing as a dark spot in the transmission image as an area including a foreign substance present on the antireflective film, and also determine, of the areas respectively appearing as the bright spots in the reflection image, an area other than the area determined as the area including the foreign substance as an area including a pinhole formed in the antireflective film, and a foreign substance removing device adapted to remove the foreign substance in the area that is determined as the area including the foreign substance present on the antireflective film by the determination means of the inspection apparatus.

An invention according to a fourth aspect of the present invention is the invention according to the third aspect, wherein the foreign substance removing device includes a foreign substance removing part adapted to remove the foreign substance in the area determined as the area including the foreign substance present on the antireflective film by the determination means of the inspection apparatus by blowing gas toward the area or performing suction on the area.

An invention according to a fifth aspect of the present invention is the invention according to the fourth aspect, wherein the foreign substance removing device includes a second inspection apparatus adapted to inspect the solar cell after the foreign substance has been supposed to be removed by the foreign substance removing part, and thereby inspect whether or not a foreign substance on the antireflective film of the solar cell is present.

An invention according to a sixth aspect of the present invention is the invention according to the fifth aspect, which includes: a main conveyance path adapted to convey a solar cell to an area including the inspection apparatus; and a conveyance mechanism adapted to, between the main conveyance path and the foreign substance removing device, convey the solar cell in which it is determined by the determination means of the inspection apparatus that the area including the foreign substance is present on the antireflective film.

An invention according to a seventh aspect of the present invention is the invention according to the sixth aspect, which includes a discharge mechanism adapted to, from the main conveyance path, discharge the solar cell in which it is determined by the determination means of the inspection apparatus that the area including the pinhole formed in the antireflective film is present.

Advantageous Effects of Invention

According to the invention according to the first aspect, among defects of a solar cell, it is possible to distinguish between a foreign substance present on an antireflective film and a pinhole present in the antireflective film. In doing so, a solar cell that becomes usable by removing a foreign substance can be recognized, and therefore productivity of solar cells can be improved.

According to the invention according to the second aspect, the beam splitter adapted to guide the visible light reflected by an antireflection film of a solar cell to the reflection image measuring means, and also guide the infrared light transmitting through the solar cell to the transmission image measuring means is provided, and therefore a reflection image and a transmission image can be measured at the same time by simultaneously irradiating the infrared light and the visible light.

According to the invention according to the third aspect, it is possible to distinguish between a foreign substance present on an antireflective film and a pinhole present in the antireflective film. In doing so, a solar cell that becomes usable by removing a foreign substance can be recognized. Also, the foreign substance removing device removes a foreign substance, and thereby productivity of solar cells can be improved.

According to the invention according to the fourth aspect, by blowing gas toward an area determined as an area including a foreign substance or performing suction on the area, the foreign substance can be easily removed.

According to the invention according to the fifth aspect, the second inspection apparatus reinspects a solar cell after the foreign substance removing part has done foreign substance removing work, and therefore a foreign substance removal state can be confirm.

According to the invention according to the sixth aspect, a solar cell in which it is determined that an area including a foreign substance is present on an antireflective film can be taken out of the main conveyance path to the foreign substance removing device, and again taken in to the main conveyance path after the foreign substance has been removed.

According to the invention according to the seventh aspect, an unrepairable solar cell in which it is determined that an area including a pinhole formed in an antireflective film is present can be discharged from the main conveyance path to the outside of a production line.

DESCRIPTION OF EMBODIMENTS

Figure 1:
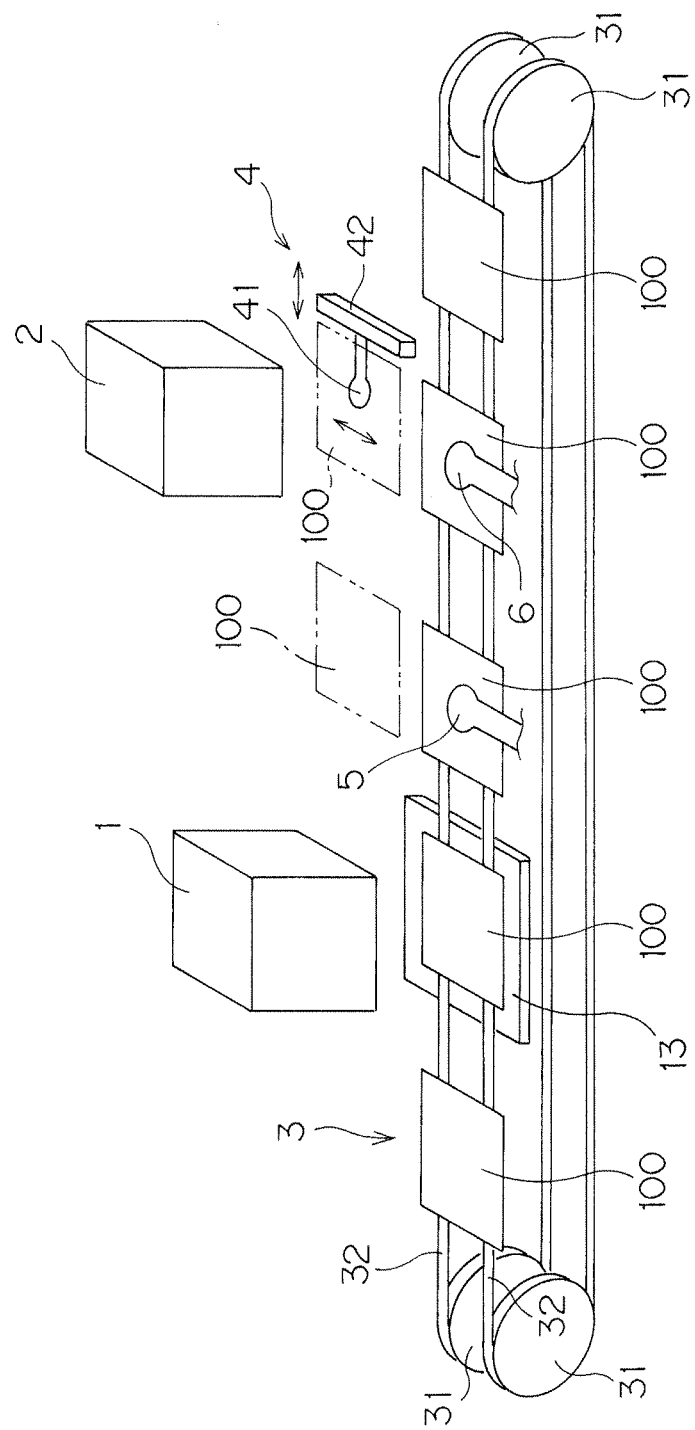
FIG. 1 is a perspective view of a processing apparatus for solar cells 100 in the present invention.
Figure 2:
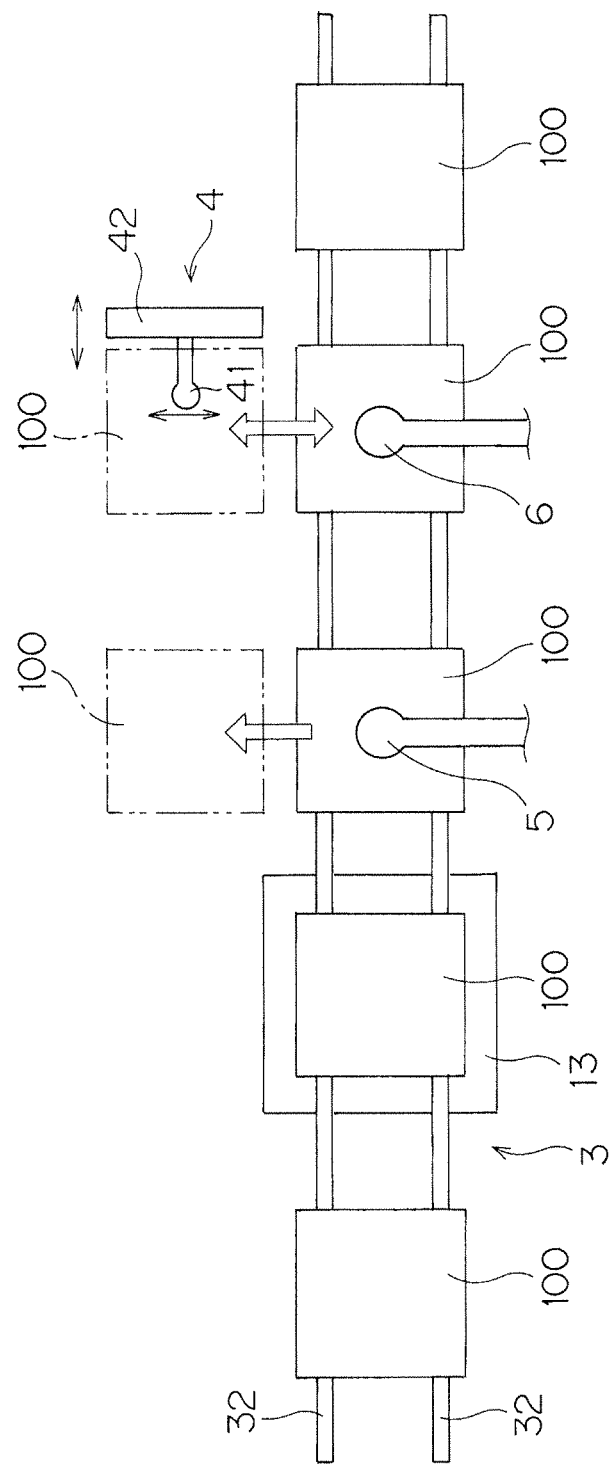
FIG. 2 is a plan view when viewed with an inspection apparatus 1 and a second inspection apparatus 2 removed from the processing apparatus for solar cells 100 in the present invention.

Embodiments of the present invention will hereinafter be described on the basis of the drawings. FIG. 1 is a perspective view of a processing apparatus for solar cells 100 in the present invention. Also, FIG. 2 is a plan view when viewed with an inspection apparatus 1 and a second inspection apparatus 2 removed from the processing apparatus for solar cells 100 in the present invention.

The processing apparatus for solar cells 100 in the present invention is for processing solar cells 100 each of which an upper surface is deposited with an antireflective film in a film deposition process in the preceding stage, and includes a conveyance device 3 adapted to form a main conveyance path for conveying the solar cells 100 to an area including the inspection device 1 with the antireflective films of the solar cells 100 directed upward. Also, the processing apparatus for solar cells 100 in the present invention includes: a foreign substance removing device 4 adapted to remove particles (foreign substances) from the solar cells; the second inspection apparatus 2 arranged above the foreign substance removing device 4; a discharge mechanism 5 adapted to, from the main conveyance path, discharge a solar cell 100 in which a pinhole is formed in the antireflective film; and a conveyance mechanism 6 adapted to take out of the main conveyance path a solar cell 100 in which a pinhole is formed in the antireflective film, and also take in to the main conveyance path a solar cell 100 in which a particle on the antireflective film is removed by the foreign substance removing device 4.

The conveyance device 3 is configured to include: four pulleys 31 on which a pair of conveyance belts 32 are wound; and an unillustrated motor that rotationally drives the pulleys 31. Also, the foreign substance removing device 4 includes a foreign substance removing part 41 adapted to remove a particle on the antireflective film of a solar cell 100 by blowing gas toward an area including the particle or performing suction on the area. The foreign substance removing part 41 is supported by a supporting member 42 movably with respect to the supporting member 42, and reciprocates in a direction orthogonal to a conveyance direction of the solar cells 100 by the conveyance device 3. Also, the supporting member 42 itself reciprocates in a direction parallel to the conveyance direction of the solar cells 100 by the conveyance device 3.

Figure 3:
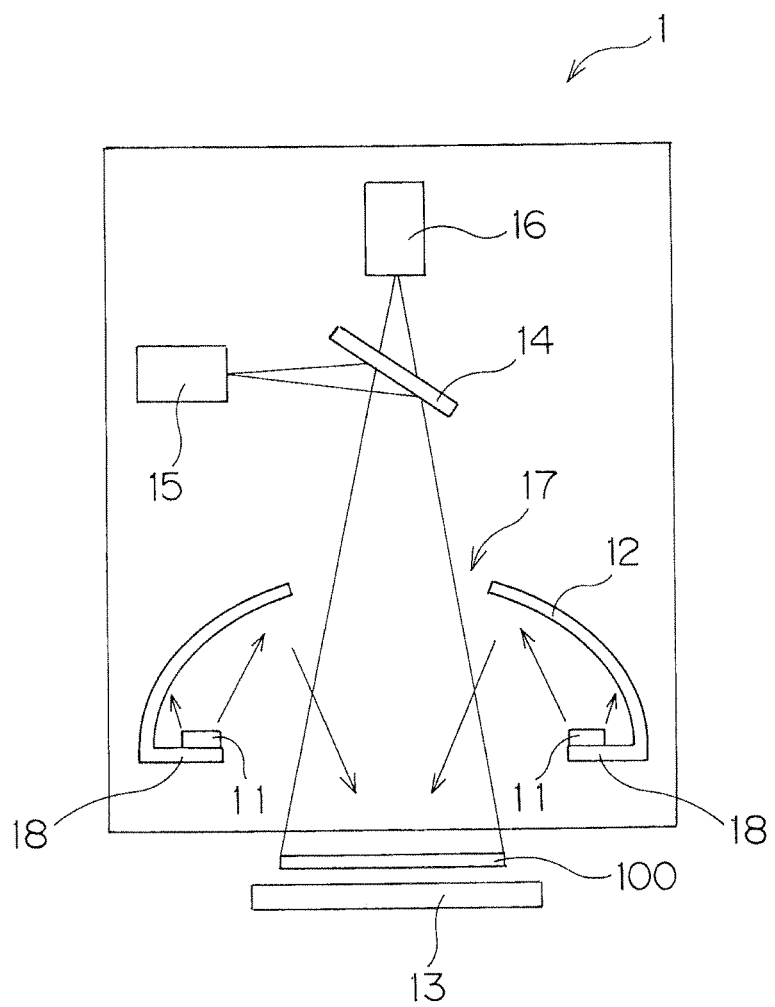
FIG. 3 is a schematic diagram of the inspection apparatus 1.
Figure 4:
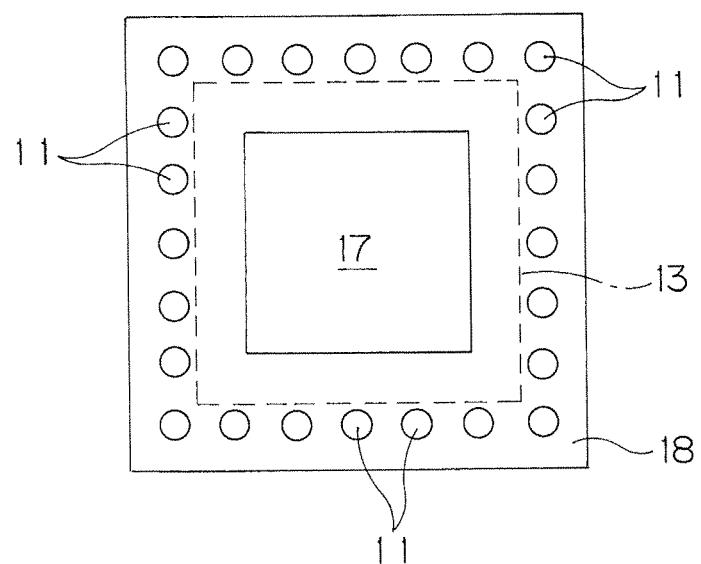
FIG. 4 is a plan view illustrating the arrangement of a plurality of light sources 11 supported by a supporting part 18.

FIG. 3 is a schematic diagram of the inspection apparatus 1. FIG. 4 is a plan view illustrating the arrangement of a plurality of light sources 11 supported by a supporting part 18. Note that in FIG. 4, an opening part 17 of a reflective diffuser plate 12 is indicated by a solid line.

The inspection apparatus 1 includes a visible light irradiation part configured to include: the plurality of visible light sources 11 that are supported by the supporting part 18 and emit visible light having a wavelength of approximately 640 nm: and the domed reflective diffuser plate 12 that is adapted to reflect the visible light irradiated from the visible light sources 11 to irradiate the upper surface of a solar cell 100, and connected to the supporting part 18. The visible light emitted from the visible light sources 11 is reflected by the reflective diffuser plate 12, and irradiated to a solar cell 100 from the antireflective film side of the solar cell 100. Note that the wavelength of the visible light is determined on the basis of the thickness and refractive index of the antireflective film so as to decrease the visible light reflectance of the antireflective film.

Also, the inspection apparatus 1 includes, as an infrared light irradiation part, an infrared light source 13 adapted to emit infrared light having a wavelength of approximately 940 nm. The infrared light emitted from the infrared light source 13 is irradiated to a solar cell 100 from the side opposite to the antireflective film of the solar cell 100. Note that the wavelength of the infrared light is determined on the basis of materials for the solar cells 100 such that the infrared light can easily transmit through the solar cells 100.

Further, the inspection apparatus 1 includes a flat plate-shaped beam splitter 14, a CCD camera 15 as reflection image measuring means, and a CCD camera 16 as transmission image measuring means. The beam splitter 14 is arranged at a position where the visible light reflected by the antireflective film of a solar cell 100 and the infrared light transmitting through the solar cell 100 are receivable. Also, the beam splitter 14 is configured to reflect the visible light and transmit the infrared light. The visible light emitted from the visible light irradiation part including the visible light sources 11 is reflected by the antireflective film of a solar cell 100, then passes through the rectangular-shaped opening 17 of the reflective diffuser plate 12, is further reflected by the beam splitter 14, and enters the CCD camera 15. On the other hand, the infrared light emitted from the infrared light source 13 transmits through the solar cell 100, then passes through the beam splitter 14, and enters the CCD camera 16.

Figure 5:
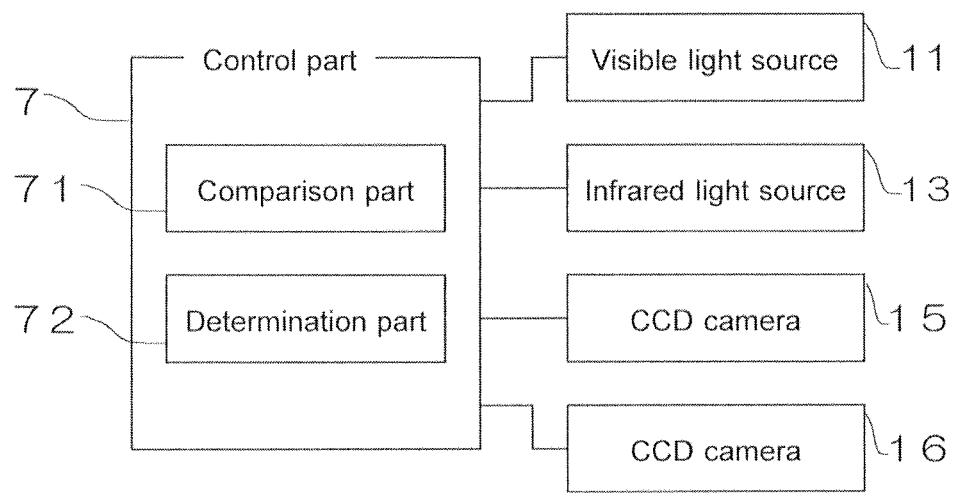
FIG. 5 is a block diagram illustrating a main control system of the inspection apparatus 1.

FIG. 5 is a block diagram illustrating a main control system of the inspection apparatus 1.

The inspection apparatus 1 includes: a CPU that performs a logical operation; a ROM that stores an operation program necessary for device control; and a RAM that temporarily stores data or the like for control, and also includes a control part 7 that controls the whole of the inspection apparatus 1. The control part 7 is connected to the above-described visible light sources 11, infrared light source 13, CCD camera 15, and CCD camera 16. Also, as will be described later, the control part 7 includes: a comparison part 71 adapted to compare a reflection image based on the visible light and a transmission image based on the infrared light with each other; and a determination part 72 adapted to determine particles on the film and pinholes in the film.

Figure 6:
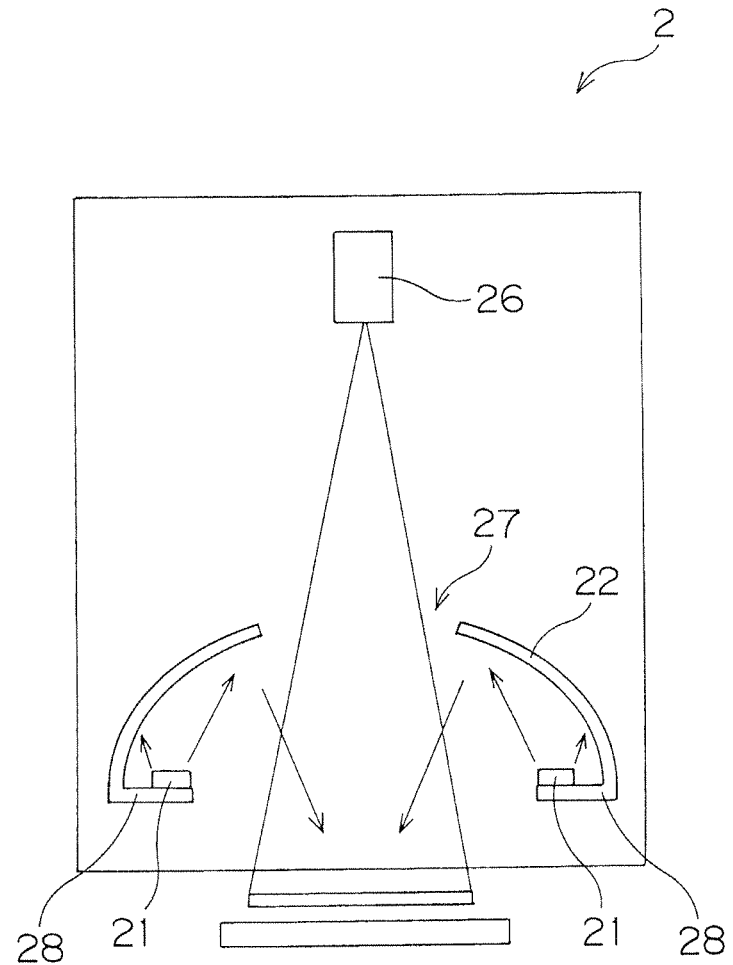
FIG. 6 is a schematic diagram of the second inspection apparatus 2.

FIG. 6 is a schematic diagram of the second inspection apparatus 2.

As with the above-described inspection apparatus 1, the second inspection apparatus 2 includes a visible light irradiation part configured to include: a plurality of visible light sources 21 that are supported by a supporting part 28 and emit visible light having a wavelength of approximately 640 nm; and a domed reflective diffuser plate 22 that is adapted to reflect the visible light irradiated from the visible light sources 21 to irradiate the upper surface of a solar cell 100, and connected to the supporting part 28. The visible light emitted from the visible light sources 21 is reflected by the reflective diffuser plate 22, and irradiated to a solar cell 100 from the antireflective film side of the solar cell 100.

Also, the second inspection apparatus 2 includes a CCD camera 26 as reflection image measuring means. The visible light emitted from the visible light irradiation part including the visible light sources 21 is reflected by the antireflective film of a solar cell 100, then passes through a rectangular-shaped opening 27 of the reflective diffuser plate 22, and enters the CCD camera 26.

In the processing apparatus for solar cells 100 having such a configuration, the solar cells 100 deposited with the antireflective film in the film deposition process in the preceding stage are conveyed by the conveyance device 3 forming the main conveyance path. Each of the solar cells 100 is conveyed to a position below the inspection apparatus 1, and at this position, as will be described later, inspected by the inspection apparatus 1 whether or not particles and/or pinholes are present on the surface thereof.

The solar cell 100 determined to have no particle or pinhole as a result of the inspection by the inspection apparatus 1 is conveyed by the conveyance device 3, and sent to the next process in the succeeding stage as is. On the other hand, the solar cell 100 in which as a result of the inspection by the inspection apparatus 1, it is determined that a pinhole is formed in the film is discharged from the conveyance device 3 forming the main conveyance path by the discharge mechanism 5. The discharge mechanism 5 is one adapted to suck and hold the solar cell 100 to discharge the solar cell 100 from the conveyance device 3 to an outside discharge part. The solar cell 100 discharged to the discharge part can be reutilized after the antireflective film including the pinhole has been removed.

Also, the solar cell 100 in which as a result of the inspection by the inspection apparatus 1, it is determined that a particle is present is taken out of the conveyance device 3 forming the main conveyance path to the foreign substance removing device 4 by the conveyance mechanism 6. The conveyance mechanism 6 is one adapted to suck and hold the solar cell 100 to take out the solar cell 100 from the conveyance device 3 to the foreign substance removing device 4 or take in the solar cell 100 from the foreign substance removing device 4 to the conveyance device 3. The foreign substance removing device 4 moves the foreign substance removing part 41 on the basis of the result of the determination by the inspection apparatus 1, and removes the particle by blowing gas toward an area including the particle on the antireflective film of the solar cell 100 or performing suction on the area.

The solar cell 100 on which the particle is supposed to be removed by the foreign substance removing device 4 is, as will be described later, reinspected by the second inspection apparatus 2 whether or not the particle is present. Then, the substrate in which it is determined by the second inspection apparatus 2 that the particle is removed is taken in from the foreign substance removing device 4 to the conveyance device 3 by the conveyance mechanism 6.

Next, an inspection process by the above-described inspection apparatus 1 is described. As illustrated in FIG. 3, for a solar cell 100 conveyed to the inspection apparatus 1 by the conveyance device 3, the antireflective film of the solar cell 100 is irradiated with the visible light emitted from the visible light irradiation part including the visible light sources 11. The visible light is reflected by the antireflective film, then further reflected by the beam splitter 14, and enters the CCD camera 15. A visible light-based reflection image measured by the CCD camera 15 is sent to the control part 7 illustrated in FIG. 5. Also, for the solar cell 100, the solar cell 100 is simultaneously irradiated with the infrared light emitted from the infrared light source 13. Subsequently, the infrared light transmits through the solar cell 100, then passes through the beam splitter 14, and enters the CCD camera 16. A transmission image measured by the CCD camera 16 is sent to the control part 7 illustrated in FIG. 5. After that, the comparison part 71 of the control part 7 compared the reflection image measured by the CCD camera 15 and the transmission image measured by the CCD camera 16 with each other.

Figure 7:
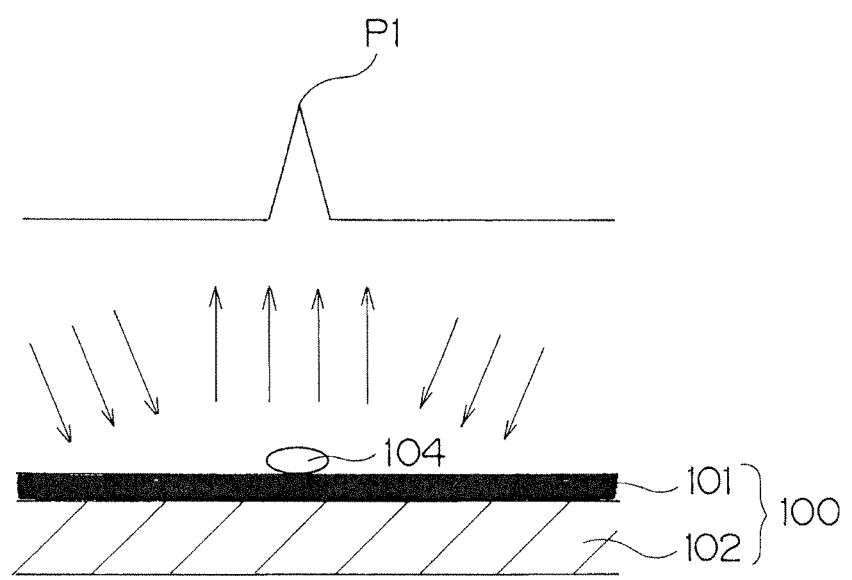
FIG. 7 is an explanatory diagram illustrating a peak P1 in a visible light-based reflection image in the case where a particle 104 is present on a solar cell 100.
Figure 8:
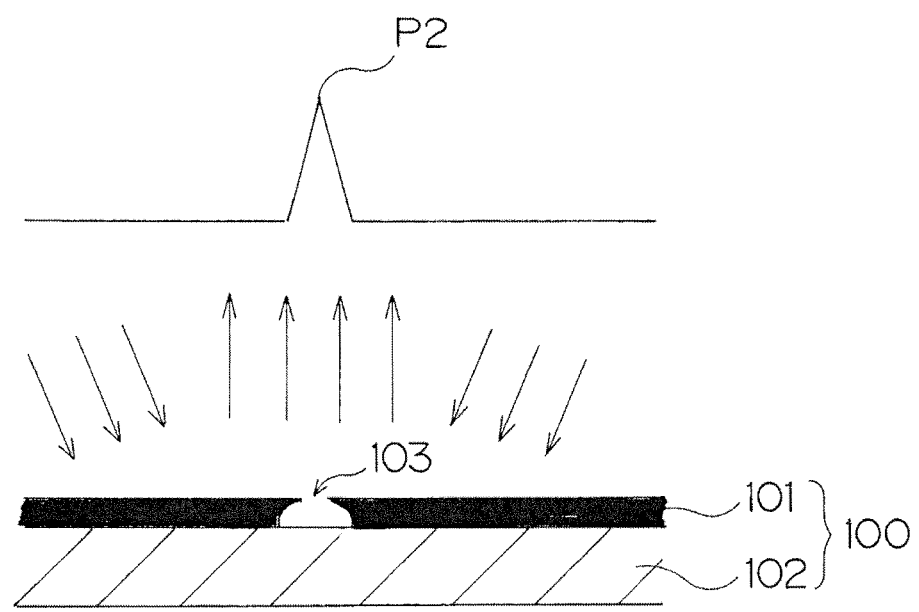
FIG. 8 is an explanatory diagram illustrating a peak P2 in a visible light-based reflection image in the case where a pinhole 103 is present in the solar cell 100.
Figure 9:
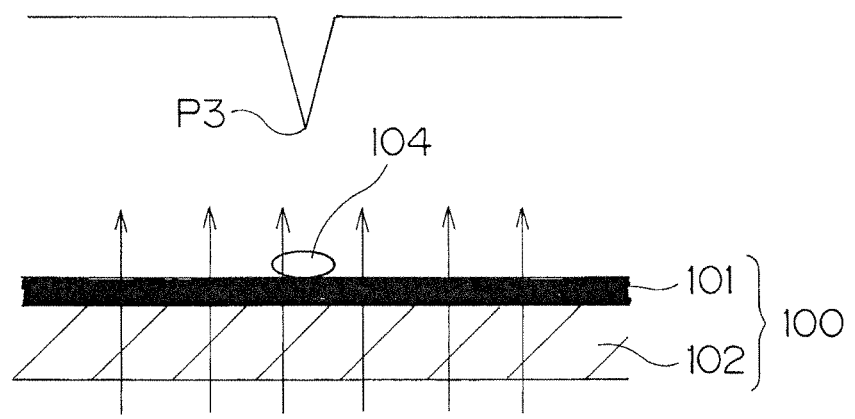
FIG. 9 is an explanatory diagram illustrating a peak P3 in an infrared light-based transmission image in the case where the particle 104 is present on the solar cell 100.
Figure 10:
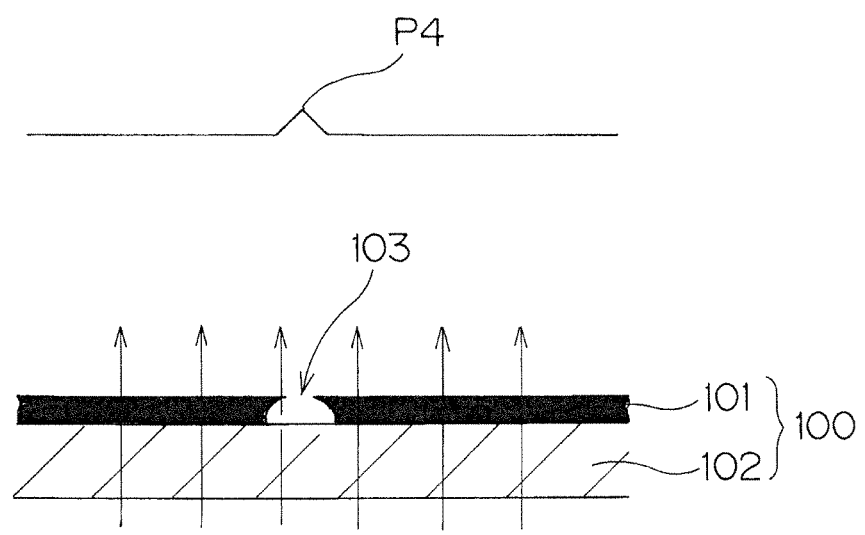
FIG. 10 is an explanatory diagram illustrating a peak P4 in an infrared light-based transmission image in the case where the pinhole 103 is present in the solar cell 100.

FIG. 7 is an explanatory diagram illustrating a peak P1 in a visible light-based reflection image in the case where a particle 104 is present on the antireflective film of a solar cell 100. FIG. 8 is an explanatory diagram illustrating a peak P2 in a visible light-based reflection image in the case where a pinhole 103 is present in the film of the solar cell 100. FIG. 9 is an explanatory diagram illustrating a peak P3 in an infrared light-based transmission image in the case where the particle 104 is present on the antireflective film of the solar cell 100. FIG. 10 is an explanatory diagram illustrating a peak P4 in an infrared light-based transmission image in the case where the pinhole 103 is present in the film of the solar cell 100. Note that in these diagrams, the antireflective film 101 and a polycrystalline substrate 102 constituting the solar cell 100 are schematically illustrated.

As illustrated in FIG. 7, in the case where the particle 104 is present on the solar cell 100, the visible light irradiated to the solar cell 100 is hardly reflected by the antireflective film 101. On the other hand, the visible light irradiated to the particle 104 is reflected by the surface of the particle 104. For this reason, in the reflection image measured by the CCD camera 15, as illustrated in FIG. 7, the peak P1 having high luminance indicating the particle 104 is recognized as a bright spot.

As illustrated in FIG. 8, in the case where the pinhole 103 is present in the film of the solar cell 100, the visible light irradiated to the solar cell 100 is hardly reflected by the antireflective film 101. On the other hand, the visible light irradiated to the pinhole 103 is reflected by the surface of the polycrystalline substrate 102. For this reason, in the reflection image measured by the CCD camera 15, as illustrated in FIG. 8, the peak P2 having high luminance indicating the pinhole 103 is recognized as a bright point.

As illustrated in FIG. 9, in the case where the particle 104 is present on the film of the solar cell 100, the infrared light transmitting through the solar cell 100 is partially blocked by the particle 104. In the transmission image measured by the CCD camera 16, as illustrated in FIG. 9, the peak P3 having low luminance indicating the particle 104 is recognized as a dark spot.

As illustrated in FIG. 10 in the case where the pinhole 103 is present in the film of the solar cell 100, the transmittance of the infrared light transmitting through the solar cell 100 is higher in the pinhole 103 area than in the antireflective film 101 area, and therefore in the transmission image measured by the CCD camera 16, as illustrated in FIG. 10, the small peak P4 having high luminance indicating the pinhole 103 is recognized as a bright spot. Note that in the case where in the solar cell 100, the thickness of the antireflective film 101 is sufficiently smaller than that of the polycrystalline substrate 102, the peak P4 is extremely small, which may not be recognizable as a bright spot.

For these reasons, by utilizing a result of comparing the reflection image measured by the CCD camera 15 and the transmission image measured by the CCD camera 16 with each other in the comparison part 71, it is possible to recognize whether a defect of the solar cell 100 is the pinhole 103 in the film or the particle 104 on the film. That is, an area appearing as a bright spot in the reflection image measured by the CCD camera 15 can be recognized as an area including some sort of defect. Specifically, of areas respectively appearing as the bright spots in the reflection image measured by the CCD camera 15, an area appearing as the dark spot in the transmission image measured by the CCD camera 16 can be determined as an area including the particle 104 present on the antireflective film 101. Also, of the areas respectively appearing as the bright spots in the reflection image measured by the CCD camera 15, an area other than the area determined as the area including the particle can be determined as an area including the pinhole 103 formed in the antireflective film 101, regardless of whether or not a bright spot is present in the transmission image measured by the CCD camera 16. Such determination is made by the determination part 72 in the control part 7 illustrated in FIG. 5.

As described above, the inspection apparatus 1 can distinguish between the pinhole 103 present in the antireflective film 101 and the particle 104 on the antireflective film 101 among defects of the solar cell 100. The solar cell 100 in which it is determined that the pinhole 103 is formed is discharged to the discharge part by the discharge mechanism 5. Also, the solar cell 100 in which it is determined that the particle 104 is present is take out to the foreign substance removing device 4 by the conveyance mechanism 6. In doing so, by removing the particle in the foreign substance removing device 4, the solar cell 100 can be recognized as a usable solar cell, and therefore productivity of solar cells 100 can be improved.

Next, an inspection process by the above-described second inspection apparatus 2 is described. As illustrated in FIG. 6, for the solar cell 100 conveyed to the foreign substance removing device 4 by the conveyance mechanism 6, the antireflective film 101 of the solar cell 100 is irradiated with the visible light emitted from the visible light irradiation part including the visible light sources 21. The visible light is reflected by the antireflective film 101, and then enters the CCD camera 26.

In the case where the particle 104 is present on the solar cell 100, the visible light irradiated to the solar cell 100 is hardly reflected by the antireflective film 101. On the other hand, the visible light irradiated to the particle 104 is reflected by the surface of the particle 104. For this reason, in the reflection image measured by the CCD camera 26, as in the above-described case illustrated in FIG. 7, the peak P1 having high luminance indicating the particle 104 is recognized as a bright spot. Accordingly, depending on the presence or absence of the bright spot, it is possible to determine the presence or absence of the particle 104.

For the solar cell 100 on which the particle 104 is determined to be present, the foreign substance removing device 4 is again used to perform the action to remove the particle 104. On the other hand, the solar cell 100 on which the particle is determined not to be present is taken in to the conveyance device 3 by the conveyance mechanism 6.

Note that the solar cell 100 in which the pinhole 103 is formed in the antireflective film 101 is discharged to the discharge part by the discharge mechanism 5, and therefore in the reflection image measured by the CCD camera 26, a bright spot indicating a pinhole 103 is never present. Note that the second inspection apparatus 2 according to this embodiment detects the particle 104 using the reflection image, but may be adapted to detect the particle 104 using a transmission image as in the case illustrated in FIG. 9.

Figure 11:
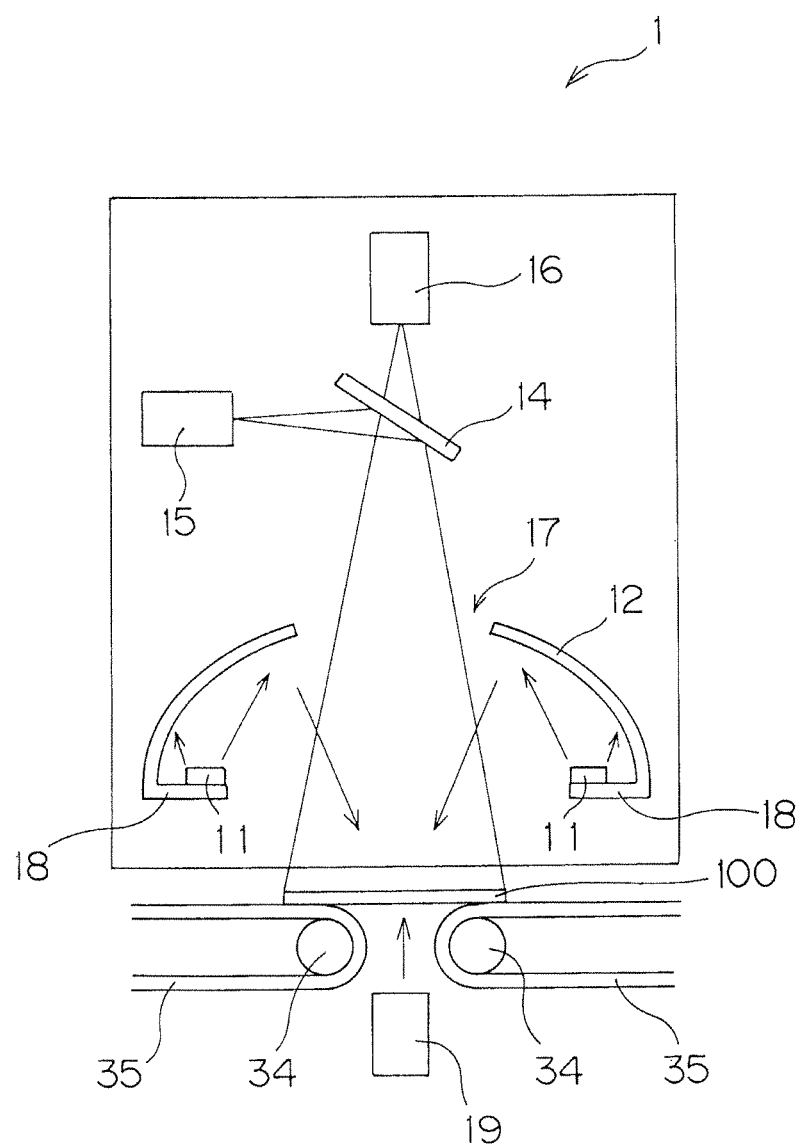
FIG. 11 is a schematic diagram of an inspection apparatus 1 according to another embodiment.

Next, another embodiment of the above-described inspection apparatus 1 is described. FIG. 11 is a schematic diagram of an inspection apparatus 1 according to another embodiment. Note that the same members in the embodiment illustrated in FIG. 3 are denoted by the same reference signs, and detailed description thereof is omitted.

In this embodiment, a pair of belts 35 that are wound on pulleys 34 to move are provided, and between the belts 35, a long-sized infrared light source 19 extending in a direction orthogonal to the conveyance direction of solar cells 100 conveyed by the belts 35 is arranged. In this embodiment, by utilizing an area between the pair of the belts 35 to irradiate a solar cell 100 with infrared light while conveying the solar cell 100 with the pair of belts 35, an infrared transparent image throughout the solar cell 100 can be obtained.

Figure 12:
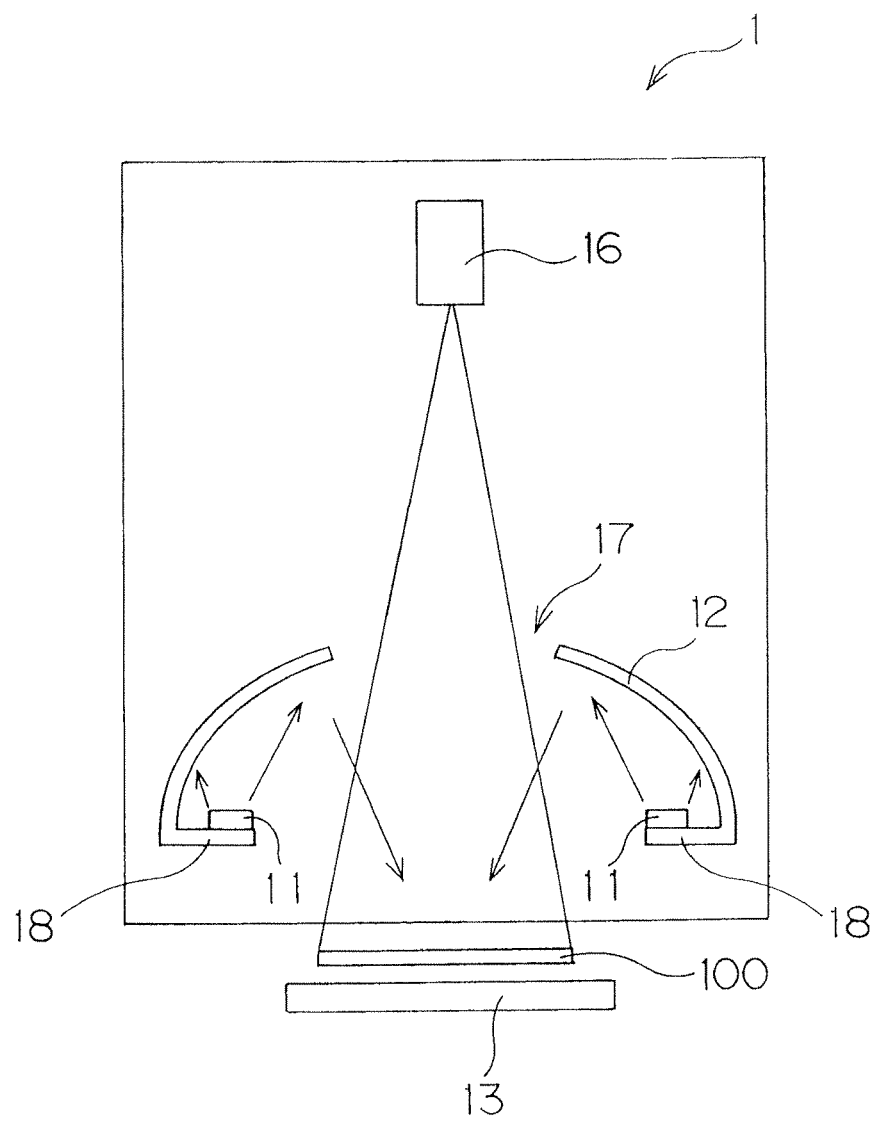
FIG. 12 is a schematic diagram of an inspection apparatus 1 according to still another embodiment.

Next, still another embodiment of the above-described inspection apparatus 1 is described. FIG. 12 is a schematic diagram of an inspection apparatus 1 according to still another embodiment. Note that the same members in the embodiment illustrated in FIG. 3 are denoted by the same reference signs, and detailed description thereof is omitted.

This embodiment is configured to omit the beam splitter 14 and CCD camera 15 in the first embodiment illustrated in FIG. 3, and to obtain a visible light-based reflection image and an infrared light-based transmission image by a single CCD camera 16. In the first embodiment illustrated in FIG. 3, a visible light-based reflection image and an infrared light-based transmission image can be imaged at the same time, and even in the case where a particle on a solar cell 100 moves with time, the particle is never erroneously determined as a pinhole. On the other hand, in the embodiment illustrated in FIG. 12, the single CCD camera 16 obtains a visible light-based reflection image and an infrared light-based transmission image at different times, and this is a low-cost system having a smaller number of device components. In this embodiment, by mutually shifting irradiation times of the visible light and the infrared light, a visible light-based reflection image and an infrared light-based transmission image can be obtained in a time division manner, and by comparing the images, it is possible to distinguish between a particle and a pinhole.

REFERENCE SIGNS LIST

1 Inspection apparatus
2 Second inspection apparatus
3 Conveyance device
4 Foreign substance removing device
5 Discharge mechanism
6 Conveyance mechanism
7 Control part
11 Visible light source
12 Reflective diffuser plate
13 Infrared light source
14 Beam splitter
15 CCD camera
16 CCD camera
17 Opening part
18 Supporting part
21 Visible light source
22 Reflective diffuser plate
26 CCD camera
27 Opening part
28 Supporting part
31 Pulley
32 Belt
34 Pulley 35 Belt
41 Foreign substance removing part
42 Supporting member
71 Comparison part
72 Determination part
100 Solar cell
101 Antireflective film
102 Polycrystalline substrate
103 Pinhole
104 Particle

The invention claimed is:

1. A solar cell inspection apparatus adapted to inspect a solar cell deposited with an antireflective film, the solar cell inspection apparatus comprising:
   visible light irradiation means adapted to irradiate visible light to the solar cell from an antireflective film side of the solar cell;
   reflection image measuring means adapted to measure a reflection image based on the visible light that is irradiated from the visible light irradiation means and reflected by the antireflective film of the solar cell;
   infrared light irradiation means adapted to irradiate infrared light from a side opposite to the antireflective film of the solar cell;
   transmission image measuring means adapted to measure a transmission image based on the infrared light that is irradiated from the infrared light irradiation means and transmits through the solar cell;
   comparison means adapted to compare the reflection image measured by the reflection image measuring means and the transmission image measured by the transmission image measuring means with each other; and
   determination means adapted to determine, of areas respectively appearing as bright spots in the reflection image, an area appearing as a dark spot in the transmission image as an area including a foreign substance present on the antireflective film, and also determine, of the areas respectively appearing as the bright spots in the reflection image, an area other than the area determined as the area including the foreign substance as an area including a pinhole formed in the antireflective film.

2. The solar cell inspection apparatus according to claim 1, wherein
   the visible light irradiation means and the infrared light irradiation means simultaneously irradiate one surface and the other surface of the solar cell with the visible light and the infrared light, respectively,
   the solar cell inspection apparatus comprising
   a beam splitter adapted to receive the visible light reflected by the antireflective film of the solar cell and the infrared light transmitting through the solar cell; guide the visible light reflected by the antireflective film of the solar cell to the reflection image measuring means, and also guide the infrared light transmitting through the solar cell to the transmission image measuring means.

3. A solar cell processing apparatus adapted to process a solar cell deposited with an antireflective film, the solar cell processing apparatus comprising
   an inspection apparatus having:
   visible light irradiation means adapted to irradiate visible light from an antireflective film side of the solar cell;
   reflection image measuring means adapted to measure a reflection image based on the visible light that is irradiated from the visible light irradiation means and reflected by the antireflection film of the solar cell;
   infrared light irradiation means adapted to irradiate infrared light from a side opposite to the antireflective film of the solar cell;
   transmission image measuring means adapted to measure a transmission image based on the infrared light that is irradiated from the infrared light irradiation means and transmitting through the solar cell;
   comparison means adapted to compare the reflection image measured by the reflection image measuring means and the transmission image measured by the transmission image measuring means with each other; and
   determination means adapted to determine, of areas respectively appearing as bright spots in the reflection image, an area appearing as a dark spot in the transmission image as an area including a foreign substance present on the antireflective film, and also determine, of the areas respectively appearing as the bright spots in the reflection image, an area other than the area determined as the area including the foreign substance as an area including a pinhole formed in the antireflective film, and
   a foreign substance removing device adapted to remove the foreign substance in the area that is determined as the area including the foreign substance present on the antireflective film by the determination means of the inspection apparatus.

4. The solar cell processing apparatus according to claim 3, wherein
   the foreign substance removing device comprises a foreign substance removing part adapted to remove the foreign substance in the area determined as the area including the foreign substance present on the antireflective film by the determination means of the inspection apparatus by blowing gas toward the area or performing suction on the area.

5. The solar cell processing apparatus according to claim 4, wherein
   the foreign substance removing device comprises a second inspection apparatus adapted to inspect the solar cell after the foreign substance has been supposed to be removed by the foreign substance removing part, and thereby inspect whether or not the foreign substance on the antireflective film of the solar cell is present.

6. The solar cell processing apparatus according to claim 5, comprising:
   a main conveyance path adapted to convey a solar cell to an area including the inspection apparatus; and
   a conveyance mechanism adapted to, between the main conveyance path and the foreign substance removing device, convey the solar cell in which it is determined by the determination means of the inspection apparatus that the area including the foreign substance is present on the antireflective film.

7. The solar cell processing apparatus according to claim 6, comprising
   a discharge mechanism adapted to, from the main conveyance path, discharge the solar cell in which it is determined by the determination means of the inspection apparatus that the area including the pinhole formed in the antireflective film is present.

* * * * *